United States Patent [19]

Liu et al.

[11] Patent Number: 6,028,198

[45] Date of Patent: Feb. 22, 2000

[54] PHARMACEUTICAL COMPOSITION FOR PREVENTION AND TREATMENT OF MOTION SICKNESS SYNDROME

[75] Inventors: Chuanhui Liu; Liuhong Yun; Guangling Wen; Fanzhong Zeng; Ruiqi Yu; Guihua Yu; Xiaoming Wang; Weixian Wang; Aiping Wang, all of Beijing, China

[73] Assignee: Institute of Pharmacology and Toxicology Academy of Military Sciences P.L.A., Beijing, China

[21] Appl. No.: 08/632,504

[22] PCT Filed: Oct. 22, 1994

[86] PCT No.: PCT/CN94/00080

§ 371 Date: Dec. 13, 1996

§ 102(e) Date: Dec. 13, 1996

[87] PCT Pub. No.: WO95/11025

PCT Pub. Date: Apr. 27, 1995

[30] Foreign Application Priority Data

Oct. 22, 1993 [CN] China .................................. 93119491

[51] Int. Cl.[7] ............................................... C07D 221/02
[52] U.S. Cl. .............................................................. 546/183
[58] Field of Search ............................ 546/183; 514/230.8

[56] References Cited

U.S. PATENT DOCUMENTS

| | | | |
|---|---|---|---|
| 4,713,391 | 12/1987 | Chiang et al. | 514/412 |
| 4,783,478 | 11/1988 | Wootton et al. | 514/397 |
| 5,034,398 | 7/1991 | King | 514/299 |
| 5,053,412 | 10/1991 | Fisher et al. | 514/278 |
| 5,073,560 | 12/1991 | Wu et al. | 514/278 |
| 5,647,835 | 7/1997 | Martineau | 600/27 |

FOREIGN PATENT DOCUMENTS 549 496   3/1986   Spain .

OTHER PUBLICATIONS

Zhang Qi–Kai, Acta Pharmaceutica Sinica, 1984, 19: 748–754.

Zhu et al., 1993, Chinese J. Clin. Pharmacol. 9(2):65–74.

Spanish Patent 549,796 by Alonso and Loxano, Oct. 12, 1995.

*Primary Examiner*—Deborah C. Lambkin
*Attorney, Agent, or Firm*—Baker & Botts, L.L.P.

[57] ABSTRACT

The present invention involves a pharmaceutical composition for preventing and treating motion sickness syndrome, the method of using it to treat motion sickness syndrome and the method for preparing phencynonate hydrochloride of α-configuration, the active component of the pharmaceutical composition. As compared with the known anti-motion sickness drugs, the pharmaceutical composition of the present invention showed higher efficacy and lower side effects. In addition, the pharmaceutical composition of the present invention can also be used for preventing and treating many symptoms of functional disorders of central and peripheral cholinergic system resulting from excessive central and peripheral acetyl choline.

3 Claims, No Drawings

PHARMACEUTICAL COMPOSITION FOR PREVENTION AND TREATMENT OF MOTION SICKNESS SYNDROME

This application is a 371 of PCT/CN94/00080 Oct. 22, 1994.

The present invention relates to a pharmaceutical composition for prevention and treatment of motion sickness syndrome, the method of its use in the treatment of motion sickness syndrome and a process of preparation of phencynonate hydrochloride as the active component of this pharmaceutical composition.

The motion sickness syndrome is a special syndrome occurring in man under the circumstances of motion, bump or rotation. Its main manifestations are dizziness, pallor, cold sweat, nausea and vomiting. The motion sickness syndrome is frequently seen in the operators and passengers of spacecrafts, seagoing vessels, automobiles and trains. According to the statistics, on an average, 10–30% of the persons during common sea voyage, 1% of the persons during civil aviation and 50–60% of the persons during space flight have motion sickness syndrome in varying degrees. The pathogenesis of motion sickness syndrome is still being studied further, but at present, the recognized chief pathogenesis is a series of central and peripheral cholinergic hyperfunction resulting from hyperexcitation of vestibular cholinergic system of man stimulated by the motion environment.

For many years, extensive researches have been carried out for prevention and treatment of motion sickness syndrome and some drugs have been developed. These drugs can be divided mainly into two groups, i.e. central anticholinergics and antihistamines. The representative drug is scopolamine. Although the drugs of these two groups have certain therapeutic effectiveness at their effective dosages, the side effect somnolence to a certain degree is present. Somnolence is a serious potential threat to the operators of spacecrafts, airplanes, seagoing vessels, vehicles and ships, such as being a hidden danger of accident, and also brings about much inconvenience to the passengers or tourists taking these drugs, such as causing lassitude. It is therefore, still necessary to develope an anti-motion sickness drug with high therapeutic effectiveness and minimal side effects.

The object of the present invention is to find an anti-motion sickness drug having high anti-motion sickness effectiveness and minimal side effects, i.e. enabling the patient to keep clear mind while maintaining the anti-motion sickness effectiveness, and overcoming the most obvious side effect of the available anti-motion sickness drugs-somnolence.

Through extensive and deepgoing researches, the inventor found unexpectedly that the pharmaceutical composition containing phencynonate hydrochloride of α-configuration [3-methyl-3-azabicyclo (3, 3, 1) nonan-9 α-yl-2-phenyl-2-cyclopentyl-2-hydroxy-acetate] shown in following formula (I) as the active component had excellent anti-motion sickness effectiveness and obviously lower side effect than all the known anti-motion sickness drugs. The present invention was accomplished on the basis of the above finding.

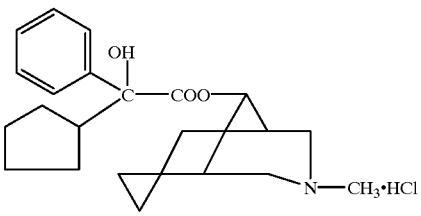

(I)

The Spanish patent No. 549496 reported a process of preparation of mandelic acid (hydroxy phenylacetic acid) derivatives. Although the compounds prepared by this process contained 3-methyl-3-azabicyclo (3, 3, 1) nonan-9-yl-2-cyclopentyl 2-hydroxy phenylacetate, the spatial configuration of azabicyclic ester was not involved and their effectiveness in treatment of motion sickness syndrome was not mentioned. Moreover, Zhang Qi-Kai and associates reported the synthesis and anticholinergic activity of a series of α and β isomers of 3-methyl-3-azabicyclo (3, 3, 1) nonan-9-yl esters in Acta Pharmaceutica Sinica 1984, 19:748–754, but they did not report the structure of the compound involved in the present invention.

The first object of the present invention relates to the pharmaceutical composition containing phencynonate hydrochloride of α-configuration in formula I as the active component, which has excellent anti-motion sickness efficacy and obviously lower side effect (such as somnolence) than all known anti-motion sickness drugs.

According to the present invention, the pharmaceutical composition of the present invention has excellent efficacy in prevention and treatment of motion sickness syndrome with total effective rate higher than 80% in prevention of carsickness and seasickness. In regard to the efficacy in reducing the changes of electronystagmogram caused by acceleration of rotation and the changes of electrogram of body of stomach and gastric antrum caused by Coriolis acceleration, the pharmaceutical composition of the present invention could reduce significantly the changes of the above indices with p value <0.01 by statistical treatment, while the placebo control group had no change in above indices. In respect to the main side effect somnolence, the incidence of somnolence after administration of the pharmaceutical composition of the present invention for prevention of carsickness and seasickness was 10%, that after diphenidol was 18.7%, p<0.05, and after placebo was 22.4%, p<0.01.

Furthermore, the pharmaceutical composition of the present invention has high biological activity on central and peripheral cholinergic receptors. For examples, its potency in antagonizing the central tremor induced by arecoline, a M agonist, is 1.1 times higher than that of atropine and that in antagonizing the central convulsion induced by nicotine, a N agonist, is 6.7 times higher than that of atropine; it has good effectiveness in antagonizing the convulsion induced by soman, a cholinesterase inhibitor, while atropine has no such action; its potency in dilating the pupil, inhibiting the salivary secretion and central inhibition is 1/13, 1/8 and 1/4 of that of scopolamine respectively.

Therefore, the pharmaceutical composition of the present invention has obvious anti-motion sickness effectiveness, while its side effect (mainly somnolence) is significantly lower than that of the known drugs.

The second object of the present invention is directed to the preparations of the pharmaceutical composition of the present invention and their preparing process. The pharmaceutical composition of the present invention can be treated with the conventional methods for preparing the pharmaceutical preparations in this art by mixing the compound of formula (I) and the excipients or carriers commonly used in pharmaceutical art to form the dosage forms needed. According to the present invention, the pharmaceutical composition of the present invention can be processed to form tablet, capsule, sustained releasing patch, chewing gum, injection in which the tablet is preferred. According to the present invention, the pharmaceutical composition of the present invention contains 0.05%–7% (by weight) of the formula (I) compound.

The third object of the present invention relates to the method of use of the pharmaceutical composition of the present invention for prevention and treatment of the motion sickness syndrome. The method includes administering the pharmaceutical composition of the present invention to the patients requiring prevention and treatment. The routes of administration include oral administration, patch sticking, intramuscular injection and oral administration is recommended preferentially. For example, 1 tablet of the pharmaceutical composition of the present invention can be administered orally half an hour before motion. Each tablet contains formula (I) compound 1–4 mg and its action lasts 4–5 h.

The further object of the present invention relates to a process for preparing the formula (I) compound. Said process includes:

(i) reacting the formula (II) compound (the R in the formula is $CH_3$, $C_2H_5$) with the formula (III) compound in the inert solvent in the presence of alkaline catalyst, followed by addition of hydrochloric acid, or

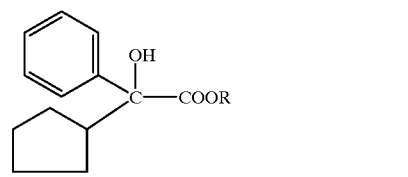

(II)

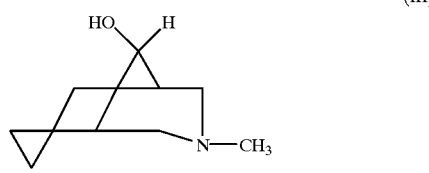

(III)

(ii) reacting the formula (IV) compound with formula (III) compound in the inert solvent in the presence of carbonyl diimidazole, followed by addition of hydrochloric acid.

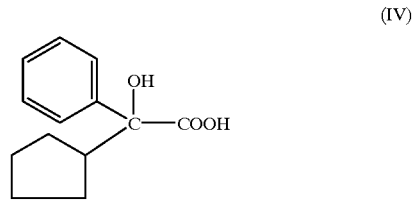

(IV)

According to the process in the present invention, the alkaline catalyst in (i) was selected form sodium hydride, metal sodium, sodium methoxide or sodium ethoxide. The formula (II) compound can be prepared by the known method [See U.S. Pat. No. 3,381,017 (1968)] and the formula (III) compound can also be prepared by the known method [See House H.O. et al: J. Org. Chem. 28,2407 (1983)]. The molar ratio of formula (II) compound and formula (III) compound is 1:1–1:5 and the reaction temperature is 20–100° C.

The following examples are used to describe further the present invention in detail, but it showd be made clear that these examples do not mean any restriction on the present invention.

EXAMPLE 1

Synthesis of 9 α-[3-methyl-3-azabicyclo (3, 3, 1) nonanyl-2-phenyl-2-cyclopentyl-2-hydroxy-acetate hydrochloride:

(1) 228 g (0.974 mol, $n_D^{25}$ 1.5205) of Methyl 2-phenyl-2-cyclopentyl-2-hydroxy-acetate, 141 g (0.910 mol, mp 94–5° C.) of 3-methyl-3-azabicyclo (3, 3, 1) nonan-92-01, 2500 ml of anhydrous n-heptane 2500 ml and sodium hydride (8.2 g, assay 80%) were added successivehy into a 5-liter three-necked flask the mixture was heated in an oil bath with stirring to distil out methanol slowly. After reaction for 3 h, the solvent was removed under reduced pressure and the mixture was cooled at room temperature. 2 N hydrochloric acid was added dropwise with stirring and a white solid was isolated. After filtration, the solid obatined was washed with ice water after drying by pressing, dried in air and recrystallized form 95% ethanol 800 ml. After filtration and drying, 232 g of 9 α-[3-methyl-3-azabicyclo (3, 3, 1) nonanyl-2-phenyl-2-cyclopentyl-2-hydroxyacetate hydrochloride, was obtained in 65% yield, mp 202–5° C. (decomposing while metting).

Element analysis: $C_{22}H_{31}NO_3HCl=393.93$

Calculated value %: C 67.07; H 8.19; N 3.56; Cl 9.01;

Found value %, C 67.00; H 8.08; N 3.46; Cl 8.93

Infrasred spectra (IR): KBr, $cm^{-1}$ 3400; 1730; 1600; 1240.

Ultraviolet spectra (UV) $\lambda_{max}$ 257.6 ($\epsilon$234, $H_2O$)

$^1H$ nuclear magnetic resonance spectra ($^1H$ NMR), $CDCl_3$, δ, TMS, 10.96 (s, b, 1 H), 7.63 (d, 2 H, J=7), 7.36 (t, 1 H, J=7), 7.28 (m, 2 H, J=7), 4.97 (s, 1 H), 3.82 (d, 1 H, J=12.7), 3.87 (d, 1 H, J=12.7), 3.20–3.02 (m, 3 H), 2.88 (d, 3 H, J=4.4), 2.28–1.36 (m, 16 H).

| $^{13}CNMR$, CDC 13, δ, | |
|---|---|
| 175.14 1C | 31.58 1C |
| 141.18 1C | 31.16 1C |
| 128.28 2C | 26.96 1C |
| 127.83 1C | 26.64 1C |
| 126.00 2C | 26.52 1C |
| 79.40 1C | 26.10 1C |
| 72.01 1C | 22.90 1C |
| 58.59 1C | 22.55 1C |
| 47.67 1C | 17.94 1C |
| 46.41 2C | |

Mass spectrogram (MS) m/z 357 ($M^+$)

(2) Using the same procedure as described in example 1 above, the differences were adding successively 18 g (0.0654 mol) of methyl 2-phenyl-2-cyclopentyl-2-hydroxy-acetate 10 g (0.0646 mol) of 3-methyl-3-azabicyclo (3, 3, 1) nonan-9 α-o 1, 250 ml of n-heptane and replacing sodium hydride by 0.2 g (0.0087 mol) of metal sodium. 7.6 g of the target compound was obtained in 29.8% yield, mp 202–204° C. (decomposing while melting). The data of infrared and nuclear magnetic resonance spectra were same as those in (1) above.

(3) Using the same method as described for (1) above the differences were adding successively 20 g (0.0858 mol) of methyl 2-phenyl-2-cyclopentyl-2-hydroxy-acetate, 11 g (0.0715 mol) of 3-methyl-3-azabicyclo (3, 3, 1) nonan-9 α-o 1, 300 ml of n-heptane and replacing sodium hydride by 0.03 mol sodium methoxide 1.62 g. 17.2 g of the target compound was obtained in 61% yield, mp 202–4° C. (decomposing while melting). The data of infrared and nuclear magnetic resonance spectra were same as those in (1) above.

(4) Using the same method as described for (1) above, the differences were adding successively 5 g (0.0214 mol), of methyl 2-phenyl-2-cyclopentyl-2-hydroxy-acetate 2.76 g(0.078 mol) of 3-methyl-3-azabicyclo (3, 3, 1) nonan-9 α-o 1 0.534 g (0.0178 mol) of 80% sodium hydride and replacing n-heptane by 150 ml of anhydrous toluene. 3.0 g of the target compound was obtained in 42.5% yield, mp 202–4° C. (decomposing while melting). The data of infrared and nuclear magnetic resonance spectra were same as those in (1) above.

(5) Using the same method as described for (1) above, the differences were adding successively 5 g (0.0214 mol) of methyl 2-phenyl-2-cyclopentyl-2-hydroxy-acetate 2.76 g (0.78 mol) of 3-methyl-3-azabicyclo (3, 3, 1) nonan-9 α-o 1 and 0.534 g (0.0178 mol) of 80% sodium hydride and replacing n-heptane by 150 ml of anhydrous benzene. 4.0 g the target compound was obtained in 57% yield, mp 202–4° C. (decomposing while melting). The data of infrared and nuclear magnetic resonance spectra were same as those in (1) above

EXAMPLE 2

Peparation of Phancynonate Hydrochloride of 2-configuration:

(1) 0.7 g (0.00318 mol, mp 144–6° C. ) of 2-phenyl-2-cyclopentyl-2-hydroxy-acetic acid, 0.33 g (0.00318 mol, mp 94–5° C. ) of 3-methyl-3-azabicyclo (3, 3, 1) nonan-9 α-o 1, 0.515 g (0.0318 mol) of carbonyl diimidazole, 30 ml of anhydrous tetrahydrofuran were added into a 50-ml reaction flask. The mixture was stirred for 24 h at room temperature and the solvent was recovered under reduced pressure to give an oily residue which was separated by silicagel column chromatography. The columm was cluted with mixed solvent of chloroform, methanol and ammonia water (85:14:1). The solvent in eluate was recovered. After the residue was dissolved in ether, an appropriate amount of 2 N hydrochloric acid was added to isolate the solid, which was recrystallized from 95% ethanol to give 0.639 g of phencynonate hydrochloride in 51% yield, mp 203–5° C. (decomposing while melting). The data of infra-red spectra and muclear magnetic resonance spectra were same as those in (1) of example 1.

Element analysis: $C_{22}H_{31}NO_3HCl=393.93$

Calculated value %: C 67.07; H 8.19; N 3.56

Found value %: C 67.24, H 8.29; N 3.45

(2) Using the same method as described for (1) of example 2, raw materials of equal weight were addcd successively. The difference was replacing tetrahydrofuran by anhydrous dimethyl formamide (DMF). 0.542 g of phencynonate hydrochloride of 2-configuration was obtained in 43.3% yield, mp 203–5C. (decomposing while melting). The data of infra-red spectra and nuclear mafnetic resonance spectra were same as those in (1) of example 1.

EXAMPLE 3

(1) Preparation of methyl 2-phenyl-2-cyclopentyl-2 hydroxy acetate:

22 g (0.90 mol, grade 4) of magnesium filings and 250 ml of absolute ether were added into a three-necked flask. 110 g (1.0 mol, grad 3) of ethyl bromide in 250 ml of absolute ether solution were added dropwise to form Grignard reagent. Dry nitrogen gas was bubbled and ether was evaporated. When te inner temperature rose to 60° C., 200 ml of anhydrous toluene was added and ether was distilled continuously until the inner temperature rose to 95° C. 60 g (0.9 mol) of Cyclopentadiene (industrial grade, freshly distilled, boiling point 40–41° C. ) in 250 ml of anhydrous toluene solution were added dropwise with stirring. After addition the temperature was reduced to 80° C. and distilling apparatus was used. 20 ml of ether was added and the mixture was distilled to inner temperature rising to 100° C. After cooling the reaction mixture to −5–0° C., toluene solution of 82 g (0.50 mol) of methyl phenylglyoxylate was added dropwise. After addition, the reaction mixture was stirred for 10 min and ice bath was removed, followed by stirring for 50 min at room temperature (21–23° C.) and cooling. 300 ml of 30% acetic acid and 25 ml of concentrate hydrochloric acid were added dropwise with stirring to dissolve all solid. The toluene layer was separated and washed successively with water, sodium bicarbonate solution and water. The toluene solution was transferred into a hydrogenator and 20 g of T-1-type Raney nickel was added. Reaction proceeded at room temperature until hydrogenation slowed down obviously. The material was taken out and fillered off the catalyst. The residue was washed with toluene. The washings and the filtrate were put together and toluene was evaporated, followed by distillation under reduced pressure. The fraction at 82–5° C./0.03 mm Hg was collected to obtain 96 g of the product in 82% yield, $n_D^{25}$ 1.5205, IR: $V_{OH}$ 3535 $cm^{-1}$, $V_{c=0}$ 1725 $cm^{-1}$.

Thin layer chromatography was used to control the quality of the product. The method was as follows: GF 254 thin layer plate; developer: 1, 2-dichloroethane; ultraviolet 254 nm fluorescence localization; main spot: Rf=0.72, without impurity spot.

(2) Using the same method as described for (1) of example 3, raw materials at equal weight were added successively. The difference was using a reaction temperature of −10–6° C. during dropuise addition of the toluene solution of 82 g of methyl phenylglyoxylate to cyclopentadiene Grignard reagent. 90 g of methyl 2-phenyl-2-cyclopentyl-2-hydroxy-acetate was obtained in 76.9% yield, $n_D^{25}$ 1.5203, boiling point 82–5° C./0.03 mmHg. Silicagel GF 254 thin layer plate; developer: 1,2-dichloroethane, ultraviolet 254 nm fluorescence localization, main spot: Rf=0.72, without impurity spot.

EXAMPLE 4

Preparation of Tablet:

2.0 g of Phencynonate hydrochloride of 2-configuration was dissolved in absolute ethanol. The solution was added slowly to a mixture of starch (3.5–5 g) and dextrin (50 g) already sifted through 80-mesh sieve. After mixing, the mixture was difted through 20-mesh nylon sieve. An appropriate amount of 50% ethanol was sprayed to form a soft material which was sifted through 20-mesh sieve and was used to prepare granules through 20-mesh sieve. The granules were dried at 50–60° C. with ventilation. Magnesium stearate was added to the dried granules and 14-mesh sieve was used to make the granules . After mixing, the granules were compressed into 6.5 mm tablet to give 2-configuration phencynonate hydrochloride tablet. Each tablet weighed 88 mg. Its dissolution rate was measured with drug dissolution apparatus model R (II) manufactured by Tianjin university and was found to be higher than 80% in 20 min.

EXAMPLE 5

The biological effect of the pharmaceutical composition of the present invention:

1. The anti-motion sickness effectiveness and side effects of the pharmaceutical composition of the present invention (in form of tablet) as compared with those of scopolamine and diphenidol:

and the ratios of $ED_{50}$ of the pharmaceutical composition of the present invention to that of diphenidol and to that of scopolamine were calculated. The results are shown in Table 1.

TABLE 1

Comparison of anti-motion sickness efficacy and side effects between the pharmaceatical composition of the present invention and its control drugs

| | | Equivalent dose ($ED_{50}$ mg/kg) | | | | |
|---|---|---|---|---|---|---|
| | | Pharmaceutical composition of present invention A | Scopolamine B | Diphenidol C | B/A | C/A |
| 1. | Anti-motion sickness efficacy | | | | | |
| | a. Preventing adversive circling syndrome in rabbits | 0.434 | 0.129 | >50 | 0.30 | >115 |
| | b. Preventing motion sickness-like syndrome in cats | 0.211 | 0.059 | 20.18 | 0.30 | 91.3 |
| 2. | Side effects | | | | | |
| | a. potentiating the effect of sub-threshold hypnotic dose of sodium pentobarbital in mice | 4.15 | 0.99 | 4.2 | 0.24 | 6.9 |
| | b. Inhibiting salivary secretion in mice | 3.74 | 0.47 | 8.0 | 0.13 | 13.6 |
| | c. Mydriatic effect in mice | 0.911 | 0.066 | 13.8 | 0.072 | 10.5 |

Rabbit model of adversive circling syndrome and cat model of motion sickness-like syndrome were used to observe the effectiveness of the pharmaceutical composition of the present invention and its control drugs, diphenidol and scopolamine, in preventing motion sickness-like syndrome. Experimental method: the rabbit (Japanese white rabbit weighing 1.7–2.6 kg) model of adversive circling syndrome was established by placing the reversible cholinesterase inhibitor diisopropyl fluorophosphate (DFP) and penetration enhancer dimethyl sulfoxide at the right common caretid artery of conscious rabbit to inhibit choline esterase in right side of brain (including vestibule) and to destroy the balance function of bilateral vestibules after these chemicals permeated into the blood, thus causing fored leftward circling movement. The cat (domestic cat weighing 1.4–3 kg) model of motion sickmess-like syndrome was established by intramuscular injection of reversible cholinesterase inhibitor eserine to conscious cat to induce motion sickness-like symptoms such as salivation, fecal and urinary incontinence, abdomen touching the ground, nausea and vomiting. Using the above animal models, the pharmaceutical composition of the present invention, diphenidol and scopolamine at three dosages of each (each dosage group consisted of 8 rabbits or cats) were given intragastrically to rabbits and/or cats respectively to prevent motion sickness-like symptoms and $ED_{50}$ values of preventive efficacy of the three drugs were measured respectively. The results are shown in Table 1. In addition, in order to assess the side effects of the pharmaceutical composition of the present invention, the above 3 drugs were tested in 3 mouse models, namely, model of potentiating the effect of subthreshold hypnotic dose of sodium pentobarbital (reflecting central inhibitory effect), model of mydriatic effect (reflecting the side effect of visual accomodation disturbance) and the model of inhibiting oxotremorine induced salivation (refecting the side effect of dry mouth). The mice used were Kunming species mice weighing 18–22 g. Five dosage groups were used for each drug and each group consisted of 10 mice of equal number for both sexes. $ED_{50}$ values of these 3 drugs were measured It can be seen clearly from Table 1 that the ratios of $ED_{50}$ of side effects of scopolamine and diphenidol to that of the pharmaceutical composition of the present invention (B/A, C/A) were smaller than the ratios of $ED_{50}$ of antimotion sickness efficacy of both control drugs to that of the pharmaceutical composition of the present invention, indicating that at equivalent anti-motion sickness dose, the side effects of the pharmaceutical composition of the present invention were milder than those of scopolamine and diphenidol.

2. Efficacy of the pharmaceutical composition of the present invention in prevention of seasickness and carsickness Using double blind, parallel, randomly controlled method, 90 sailor volunteers with history of seasickness and 165 medical worker volunteers with histary of carsickness were divided into 3 equal groups each (each group consisted of 30 persons with history of seasickness or 55 persons with history of carsickness). Thirty minutes before sailing or starting a car, the pharmaceutical composition of present invention containing pheneynonate hydrochloride of α-configuration 2.0 mg/person, placebo and diphenidol (25 mg/person) were given orally to different groups respectively. The ship sailed on the sea with grade 5 wave and grade 4 surge and the bus bumped up and down on the rough road with abrup turns for 2–4 h. The preventive efficacy was observed and the results are shown in Table 2.

TABLE 2

Efficacy of the pharmaceutical composition of the present invention, placebo and diphenidol in preventing seasickness and carsickness in a double blind, parallel, controlled trail

| Prevention efficacy | Group | pharmaceutical composition of present invention n | % | placebo n | % | Diphenidol n | % |
|---|---|---|---|---|---|---|---|
| Total effective rate | Ship | 24 | 80.0** | 0 | 0 | 23 | 76.7** |
|  | Bus | 48 | 87.3Δ | 9 | 16.4 | 35 | 63.6 |
| Siginficantly effective rate | Ship | 20 | 66.7** | 0 | 0 | 20 | 66.7** |
|  | Bus | 33 | 60.0** | 3 | 5.5 | 27 | 49.1** |
| Ineffective rate | Ship | 3 | 10.0** | 27 | 90.0 | 3 | 10.0** |
|  | Bus | 6 | 9.1** | 33 | 60.0 | 10 | 18.2** |

Total effective rate = significantly effective rate + effective rate
**P < 0.01, compared with placebo;
ΔP < 0.05, compared with diphenidol.

It can be seen from Table 2 that like the positive control diphenidol, the total effective rate, significantly effective rate and ineffective rate of the pharmaceutical composition of the present invention were significantly different from those of the placebo group (P<0.01), but the total effective rate of the pharmaceutical composition of the present invention in preventing carsickness was 87.3% which was higher than 63.6% in diphenidol group with P<0.05 by statistical treatment.

3. Efficacy of the pharmaceutical composition of the present invention in preventing the changes in electronystagmogram induced by revolving chair and the changes in electrogastrogram induced by Coriolis acceleration stimulation.

Using the double-blind parellelly controlled experimental method and oral administration of same doses of the 3 drugs as described for "2" 1 h before rotation, 90 volunteers divided into 3 drug groups underwent revolving chair rotation test and Coriolis acceleration test in laboratory. Rotation of the revolving chair was accelerated from 0 to 90°/s² at a rate of 1°/s² and the electronystagmogram was observed during and after rotation. In Coriolis acceleration test, the electrogastrograms of body and antrum of stomach were recorded for 2 min during 2 min stimulation. The results are shown in Table 3.

It can be seen from Table 3 that both the pharmaceutical composition of the present invention and the positive control drug diphenidol showed obvious efficacy in reducing the changes of electronystagmogram and amplitude of electrogastrogram in experiment on prevention of rotation effect. The statistical result of the difference between premedication and postmedication values was P<0.01 for the group receiving the pharmaceutical composition of the present invention, P<0.05 for diphemidol group and P>0.05, i.e. no significant difference, for placebogroup.

We claim:

1. A process for preparing 3-methyl-3-azabicyclo (3, 3, 1) nonan-9 α-yl-2-phenyl-2-cyclopentyl-2-hydroxy-acetate hydrochloride, comprising:

(i) reacting methyl or enthyl 2-phenyl-2-cyclopentyl-2-hydroxy-acetate of formula (II) with 3-methyl azabicyclo (3, 3, 1) nonan-9 α-ol of formula (III) at a molar ratio of 1:1–1:5 in inert organic solvent in the presence of alkaline catalyst at 50–110° C., followed by addition of hydrochloric acid, or

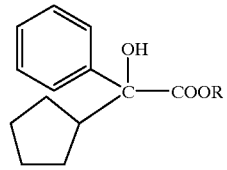

(II)

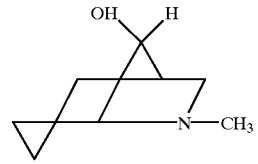

(III)

(ii) reacting 2-phenyl-2-cyclopentyl-2-hydroxy-acetic acid of formula (IV) with 3-methyl-3-azabicyclo (3, 3, 1)-nonan-9 2-ol of formula (III) at a molar ratio of 1:1–1:5 in inert organic solvent in the presence of catalyst carbomyl diimidazole at 20–100° C., followed by addition of hydrochloric acid;

TABLE 3

Efficacy of the pharmaceutical composition of the present invention in preventing changes in electronystagmogram induced by revolving chair and changes in electrogastrogram induced by coriolis acceleration stimulation

| Drug | Group | Nystagmus during rotation (degree/s) | Nystagmus after rotation (degree/s) | Amplitude of electrogastrogram of body of stomach ($\mu V$) | Amplitude of electrogastrogram of antrum of stomach ($\mu V$) |
|---|---|---|---|---|---|
| Pharmaceutical composition of present invention | Premedication | 10.2 ± 3.3 | 18.5 ± 8.5 | 540 ± 304 | 539 ± 301 |
|  | Postmedication | 6.6 ± 2.6** | 11.2 ± 6.2** | 346 ± 178** | 369 ± 184** |
| Placebo | Premedication | 8.7 ± 4.1 | 17.2 ± 5.5 | 506 ± 212 | 518 ± 216 |
|  | Postmedication | 7.6 ± 3.9 | 15.8 ± 5.5 | 457 ± 246 | 457 ± 257 |
| Diphenidol | Premedication | 8.9 ± 3.6 | 15.9 ± 6.2 | 563 ± 329 | 559 ± 333 |
|  | Postmedication | 6.9 ± 3.4* | 11.2 ± 6.2* | 396 ± 227* | 414 ± 265* |

*P < 0.05,
**P < 0.01, compared with premedication.

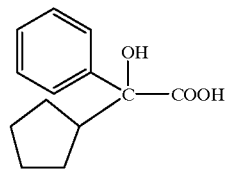
(IV)
2. The process as claimed in claim 1, in which the alkaline catalyst in (i) is selected fom the group consisting of sodium hydride, metal sodium, sodium methoxide or sodium ethoxide.
3. The process as claimed in claim 1, in which the inert organic solvent is selected from a group consisting of n-heptane, benzene, toluene, retrahydrofuran or dimethyl formamide.
* * * * *